US009655499B2

(12) United States Patent
Erden et al.

(10) Patent No.: US 9,655,499 B2
(45) Date of Patent: May 23, 2017

(54) MINIATURIZED SCANNING SYSTEM (71) Applicants: Mauna Kea Technologies, Paris (FR); EndoControl, La Tronche (FR); Université Pierre et Marie Curie, Paris (FR); Centre National de la Recherche Scientifique—CNRS, Paris (FR)

(72) Inventors: Mustafa Suphi Erden, Paris (FR); Benoit Rosa, Malakoff (FR); Jérôme Szewczyk, Vienne-en-Arthies (FR); Guillaume Morel, Malakoff (FR); Clément Vidal, Grenoble (FR); Patrick Henri, Bois Colombes (FR); Nicolas Boularot, Champigny-sur-Marne (FR)

(73) Assignees: Mauna Kea Technologies, Paris (FR); EndoControl, La Tronche (FR); Universite Pierre Et Marie Curie, Paris (FR); Centre National De La Recherche Scientifique-CNRS, Paris (FR)

( * ) Notice: Subject to any disclaimer, the term of this patent is extended or adjusted under 35 U.S.C. 154(b) by 102 days.

(21) Appl. No.: 14/394,241

(22) PCT Filed: Apr. 8, 2013

(86) PCT No.: PCT/IB2013/001024
§ 371 (c)(1),
(2) Date: Oct. 13, 2014

(87) PCT Pub. No.: WO2013/153448
PCT Pub. Date: Oct. 17, 2013

(65) Prior Publication Data
US 2015/0057499 A1    Feb. 26, 2015

Related U.S. Application Data (60) Provisional application No. 61/623,985, filed on Apr. 13, 2012.

(51) Int. Cl.
A61B 1/06    (2006.01)
A61B 1/00    (2006.01)
(Continued)

(52) U.S. Cl.
CPC ........ *A61B 1/0057* (2013.01); *A61B 1/00133* (2013.01); *A61B 1/00165* (2013.01);
(Continued)

(58) Field of Classification Search
CPC .............. A61B 1/0057; A61B 1/00133; A61B 1/00165; A61B 1/00172; A61B 5/0062
(Continued)

(56) References Cited

U.S. PATENT DOCUMENTS

2001/0055462 A1    12/2001    Seibel
2005/0242298 A1    11/2005    Genet et al.
(Continued)

FOREIGN PATENT DOCUMENTS

EP    1142529 A1    10/2001
JP    S63122417 A    5/1988
(Continued)

OTHER PUBLICATIONS

International Search Report for corresponding International Application No. PCT/IB2013/001024, mailed Oct. 1, 2013 (2 pages).
(Continued)

*Primary Examiner* — Timothy J Neal
(74) *Attorney, Agent, or Firm* — Osha Liang LLP (57) ABSTRACT A miniaturized scanning system to generate movement of a flexible device positioned at a distal part of a medical tool. The miniaturized scanning system includes an inner shaft with a longitudinal axis, adapted to guide said flexible device along the longitudinal axis, an abutment comprising an external surface and adapted to maintain said device, and a pusher mechanism adapted to engage with said abutment.

(Continued)

The miniaturized scanning system includes at least one end portion adapted to contact said external surface of the abutment at a contact point, wherein said end portion is configured to translate along said longitudinal axis of the inner shaft and wherein the translation of said end portion results in a bending of the device in a bending plane defined by the longitudinal axis of the inner shaft and said contact point.

20 Claims, 8 Drawing Sheets

(51) Int. Cl.
| | |
|---|---|
| *A61B 1/005* | (2006.01) |
| *A61B 5/00* | (2006.01) |
| *F21V 8/00* | (2006.01) |
| *G02B 6/04* | (2006.01) |
| *G02B 6/00* | (2006.01) |

(52) U.S. Cl.
CPC ........ *A61B 1/00172* (2013.01); *A61B 5/0062* (2013.01); *A61B 5/0084* (2013.01); *G02B 6/0008* (2013.01); *G02B 6/04* (2013.01); *A61B 5/0068* (2013.01); *G02B 2006/0098* (2013.01)

(58) Field of Classification Search
USPC .................................................. 600/104, 114
See application file for complete search history.

(56) References Cited

U.S. PATENT DOCUMENTS

| | | |
|---|---|---|
| 2008/0015445 A1 | 1/2008 | Saadat et al. |
| 2009/0041314 A1 | 2/2009 | Vercauteren et al. |
| 2010/0179386 A1 | 7/2010 | Kobayashi |
| 2011/0257486 A1 | 10/2011 | Chang et al. |

FOREIGN PATENT DOCUMENTS

| | | |
|---|---|---|
| JP | 2001-174744 A | 6/2001 |
| JP | 2010-162090 A | 7/2010 |

OTHER PUBLICATIONS

Written Opinion for corresponding International Application No. PCT/IB2013/001024, mailed Oct. 1, 2013 (7 pages).
Brain C. Becker et al.; "Semiautomated Intraocular Laser Surgery Using Handheld Instruments;" Laser in Surgery and Medicine, 42:264-273; Pittsburgh, Pennsylvania (2010) (10 pages).
Notification of Reasons for Refusal issued in corresponding Japanese Patent Application No. 2015-505029, mailed on Nov. 29, 2016 (10 pages).

MINIATURIZED SCANNING SYSTEM

BACKGROUND

Field of the of the Present Disclosure

The disclosure relates to a miniaturized scanning system to generate 2D movement of a distal part of a medical tool.

Background Art

The Applicant has developed a confocal imaging system based on a fiber bundle probe for in vivo in situ imaging of biological tissues as described for example in US Patent Application 2005/0242298 which is fully incorporated herein by reference. Such a system, also referred as a fibered confocal microscope, is for example represented schematically on FIG. 11. A laser 140 is scanned over a proximal face 112 of a fiber bundle probe 110 which is connected to a light injection module 130 via an abutment 120. The light injection module 130 comprises an objective ensuring that light from the laser is properly injected into each fiber of the fiber bundle probe. Scanning the proximal face of the fiber bundle results in a fiber per fiber injection of light and, at a distal end of the bundle 111, in a point per point illumination of an object under observation. As a consequence, each illuminated point of the observed object may re-emit light which is collected using an optical head and transported back to the proximal end 112 of the fiber bundle via the same fiber and finally transmitted to a detector through the same scanning process.

The single images acquired by fibered confocal microscopy typically cover an area of 240×200 $\mu m^2$. The smallness of the image size is due on the one hand to the necessity of a high level of resolution and, on the other hand, because the optical lenses housed in the optical head and the fiber bundle probe carrying the images are minimized for minimal invasiveness. A single image is not always large enough for a conclusive diagnostics and solutions have been developed to obtain high resolution images with a large field of view based on scanning the tissue area by moving the optical head of the imaging system and merging the collected images. US Patent Application 2009/0041314 in the name of the applicant describes image mosaicing techniques that can be used to provide efficient and complete representation of an enlarged field of view. With a mosaicing algorithm as described in US 2009/0041314, a sample scan of 3 $mm^2$ on tissue typically requires maintaining a distance of 150 $\mu m$ from a previously traced line with an approximate precision of 25 $\mu m$ for a continuous duration of approximately one minute. With manual sweeping, it is difficult to obtain this precision for such a long time. Further, manual sweeping may not provide the smoothness of the motion with minimal accelerations and/or changes of directions which are important when the surface to be scanned over is a biological tissue.

Several assisted handheld instruments are presented in the literature (see for example B. C. Becker, R. A. MacLachlan, L. A. J. Lobes, and C. N. Riviere, "Semiautomated intraocular laser surgery using handheld instruments", *Lasers in Surgery and Medicine*, vol. 42, pp. 246-273, 2010).

US 2001/0055462 from Siebel et al. describes an endoscopic image acquisition system, in which a unique optical fiber is driven across the field of view using two pairs of piezoelectric actuators, placed along the optical fiber at a distal end of the imaging system and oscillating in quadrature, thereby forcing the fiber to bend with the tip of the fiber describing a spiral. The fiber movement is driven close to the resonance frequency of the piezoelectric actuators so that large bending amplitudes can be reached. However, high resonance frequency is required to image a tissue in real time and this technique can hardly be used with heavy movable element.

The Applicant proposes herein under a miniaturized scanning system that can generate a 2D movement of a distal part of a medical tool, for example a surgical or endoscopic tool, while preserving the scanning accuracy, its reproducibility and the smoothness of the movement, and may be applied to any medical tool in which the distal part comprises a bulky movable element, e.g. a fiber bundle associated with a distal optical head, a catheter, a therapeutic device or the like.

SUMMARY OF THE CLAIMED SUBJECT MATTER

In at least one aspect, embodiments disclosed herein relate to a miniaturized scanning system to generate movement of a flexible device positioned at a distal part of a medical tool. The miniaturized scanning system comprises:
- an inner shaft with a longitudinal axis, adapted to guide said flexible device along said longitudinal axis,
- an abutment comprising an external surface and adapted to maintain said device,
- a pusher mechanism adapted to engage with said abutment and comprising at least one end portion adapted to contact said external surface of the abutment at a contact point, wherein said end portion is configured to translate along said longitudinal axis of the inner shaft and wherein the translation of said end portion results in a bending of the device in a bending plane defined by the longitudinal axis of the inner shaft and said contact point.

2D motion of the end of the flexible device can thus be obtained, possibly by actuation motors, for example electrical motors, located at a proximal part of the medical tool, i.e. apart from the part intended to intrude in the operation region when applied to a surgical or endoscopic medical tool. Further, the scanning system may be miniaturized while preserving the scanning accuracy, reproducibility and smoothness of motion of the end of the scanned device.

According to an embodiment, the abutment comprises an axially symmetric structure to be mounted around said device.

According to a further embodiment, the pusher mechanism comprises a movable sleeve with said end portion attached thereto, wherein the movable sleeve is mounted around said inner shaft and configured to rotate around said longitudinal axis of the inner shaft, the rotation of the movable sleeve resulting in a change of the contact point between said end potion and said external surface of the abutment.

Addressing the scanned surface is thus performed in a polar coordinates referential.

According to an embodiment, the movable sleeve may be configured to be simultaneously rotated around said longitudinal axis and translated along said axis.

According to an embodiment, the miniaturized scanning system may further comprise an outer shaft to be mounted around said movable sleeve, wherein said movable sleeve is coupled to an inner surface of the outer shaft to perform a helical movement with respect to said inner surface of the outer shaft.

According to an embodiment, said movable sleeve and inner surface of the outer shaft are coupled by a screw system.

According to a further embodiment, said external surface of the abutment has a conical shape calculated such that the simultaneous rotation and translation movement of the movable sleeve results in a spiral motion of an end of the device.

According to an embodiment, the miniaturized scanning system may further comprise a rotary drive mechanism of the movable sleeve around said longitudinal axis of the inner shaft.

According to an embodiment, the rotary drive mechanism comprises a toothed wheel arranged in a hollow portion of the inner shaft and a drive rod.

According to a further embodiment, the pusher mechanism comprises at least two end portions configured to translate independently.

According to an embodiment, the miniaturized scanning system may further comprise at least one driving motor to drive the at least one end portion of the pusher mechanism.

According to a further embodiment, said end portion comprises an edge configured to be tangent to the external surface of the abutment.

In a second aspect, embodiments disclosed herein relate to a robotized device comprising a flexible device to be positioned at a distal part of a medical tool and a miniaturized scanning system according to the first aspect to generate a movement of an end of said device.

According to an embodiment, said flexible device is one of an imaging device, a therapeutic device, a hollow conduit.

In a third aspect, embodiments disclosed herein relate to a medical tool comprising:
  a flexible device to be positioned at a distal part of said medical tool, and
  a miniaturized scanning system according to the first aspect to generate a movement of an end of said device.

According to an embodiment, the miniaturized scanning system comprises at least one driving motor positioned at a proximal part of the medical tool.

In a fourth aspect, embodiments disclosed herein relate to a fiber confocal microscopy system for inspecting a biological tissue comprising:
  a confocal microscope with a distal part to be in contact with a biological tissue, wherein said distal part comprises an optical head connected to an optical fiber bundle,
  a miniaturized scanning system according to the first aspect to generate a movement of said optical head.

According to an embodiment, the miniaturized scanning system comprises at least one driving motor positioned at a proximal part of the microscope.

In a fifth aspect, embodiments disclosed herein relate to a method for high resolution high field of view in vivo imaging of a biological using a confocal microscope with a distal part to be in contact with said biological tissue, wherein said distal part comprises an optical head connected to an optical fiber bundle, the method comprising:
  moving said optical head using a miniaturized scanning system according to the first aspect,
  collecting images while said optical head is being moved,
  combining the collected images.

According to an embodiment, the motion of the optical head is a spiral motion.

Other aspects and advantages of the disclosure will be apparent from the following description and the appended claims.

DETAILED DESCRIPTION

Specific embodiments of the present disclosure will now be described in detail with reference to the accompanying Figures. Like elements in the various Figures may be denoted by like numerals. Embodiments of the present disclosure relate to a miniaturized scanning system to generate movement of a flexible device positioned at a distal part of a medical tool and a robotized device comprising said miniaturized scanning system.

Figure 1:
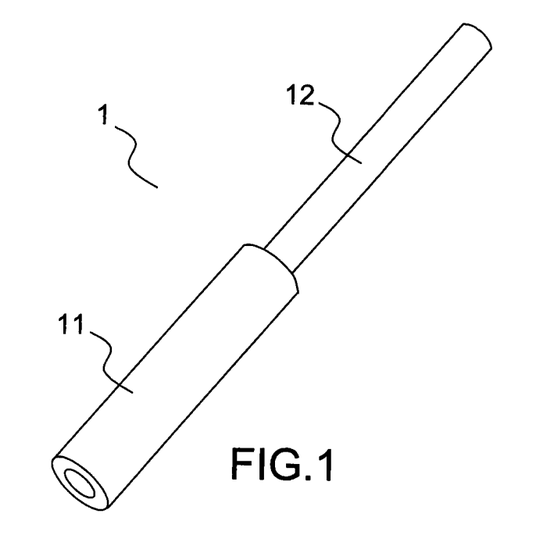
FIG. 1 represents an example of an optical probe for a medical tool.
Figure 6:
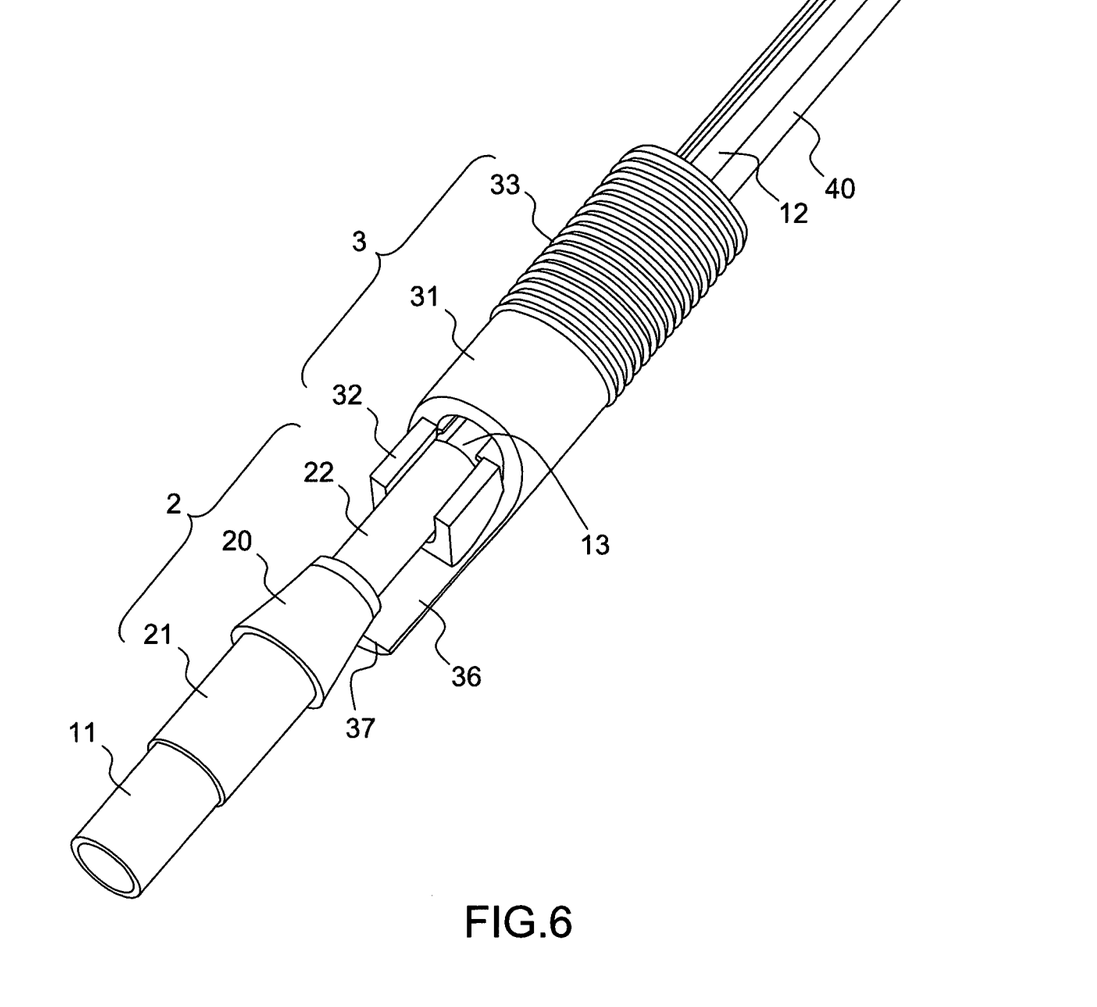
FIG. 6 represents an embodiment of a miniaturized scanning system comprising the pieces as illustrated in FIGS. 3 to 6.

FIGS. 2 to 5 represent different pieces of a miniaturized scanning system shown in FIG. 6 and adapted to generate 2D movement of an optical head 11 of an optical probe 1, an embodiment of which is shown in FIG. 1.

Figure 11:
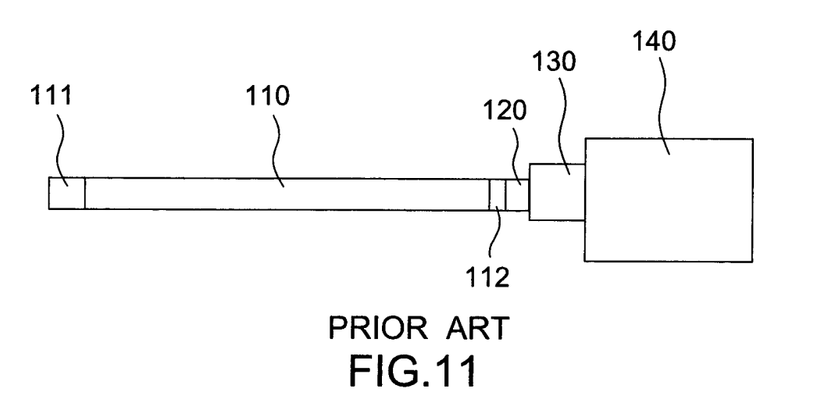
FIG. 11 schematically illustrates a fibered confocal microscope.

The optical probe 1 as shown in FIG. 1 comprises the optical head 11 which houses one or a plurality of optical lenses and the fiber cable 12 which is a flexible portion of the optical probe 1. The optical probe is for example the distal part of a fibered confocal microscope as shown in FIG. 11. The optical head 11 is typically of 2.6 mm in diameter and 1 cm in length in order to collect images of size 240×200 $\mu m^2$ with 1.2 $\mu m$ lateral and 3 $\mu m$ axial resolutions. The miniaturized scanning system as shown for example in FIG. 6 enables to scan the optical head over an area of approximately 3 $mm^2$ while keeping the overall structure built into a 5 mm inside diameter tube and provides navigation of the optical head to automatically collect images as it will be explained in detail below.

FIG. 6 represents part of a robotized (i.e., automated) optical probe 6 including the optical probe as shown in FIG. 1. In the embodiment as shown in FIG. 6, the miniaturized scanning system comprises an abutment 2, a pusher mechanism 3 and an inner shaft 4. The abutment 2, the pusher mechanism 3 and the inner shaft 4 are also represented in expanded FIGS. 2, 3, and 4, respectively.

Figure 2:
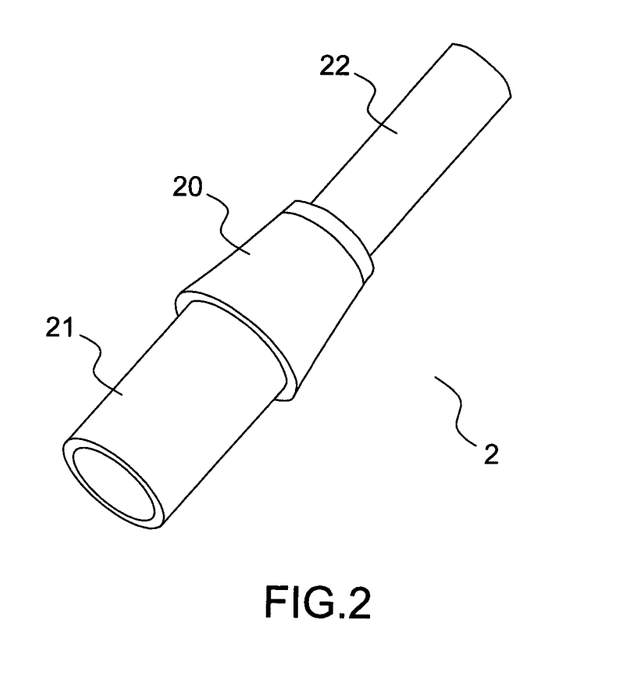
FIG. 2 represents an abutment of a miniaturized scanning system according to an embodiment.

In FIG. 2, the abutment 2 is adapted to maintain the optical probe at its distal part. In the embodiment as shown in FIG. 2, the abutment 2 comprises an axially symmetric structure to be mounted around the optical probe. The abutment 2 according to the embodiment as shown in FIG. 2 comprises a first part 21 to maintain the optical head, a second part 22 to maintain the portion of the fiber cable connected to the optical head and in between, a part with an inclined external surface 20. The external surface 20 is for example a conical shape. As it will be further explained, pushing onto the surface 20 in a direction parallel but distinct from the axis of the abutment at its nominal position will force the abutment—and thus the scanned device—to bend in a direction perpendicular to said axis.

Figure 4:
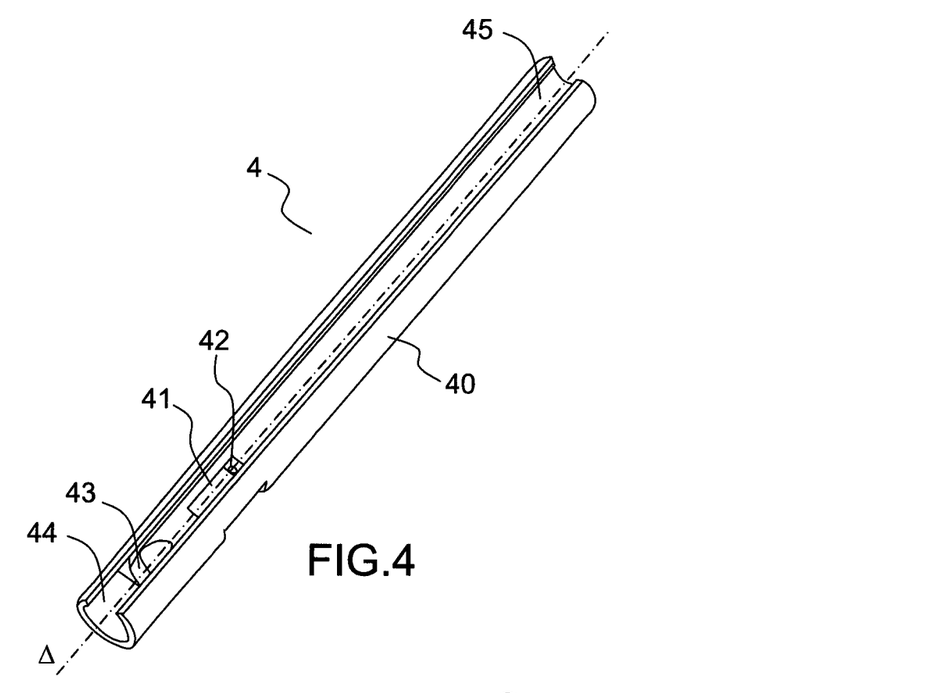
FIG. 4 represents an inner shaft of a miniaturized scanning system according to an embodiment.
Figure 5:
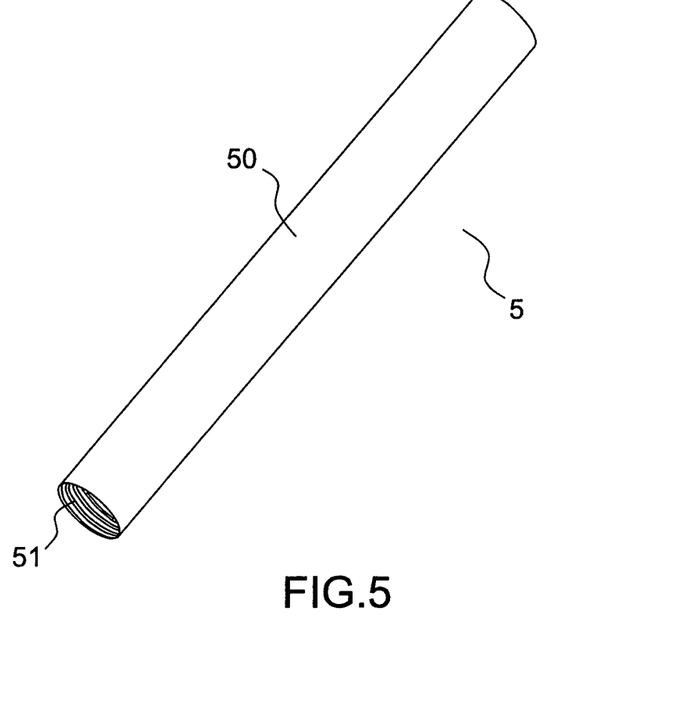
FIG. 5 represents an outer shaft of a miniaturized scanning system according to an embodiment.

The inner shaft 4 is configured to guide the optical probe. As shown in the example of FIGS. 4 and 6, the inner shaft 4 comprises a tube 40 with a groove 45 adapted to receive the optical fiber cable 12 which is the flexible portion of the optical probe. At the distal end 44 of the groove, the optical fiber cable 12 is maintained and guided along a longitudinal axis Δ of the groove. As it is apparent in FIG. 6, a portion 13 of the optical fiber cable 12 is kept free and can therefore bend when an axial force is exerted on the external surface 20 of the abutment. This portion 13 of the optical fiber cable is positioned between the part of the optical probe maintained by the abutment and the part of the optical probe fixed to the inner shaft. The length of the portion 13 may be long enough to ensure a minimal radius of curvature when bending and short enough to avoid having the portion 13 too soft. Typically, the portion 13 of the optical fiber cable may be comprised between 0.3 mm and 0.7 mm, preferably about 0.5 mm.

Figure 3:
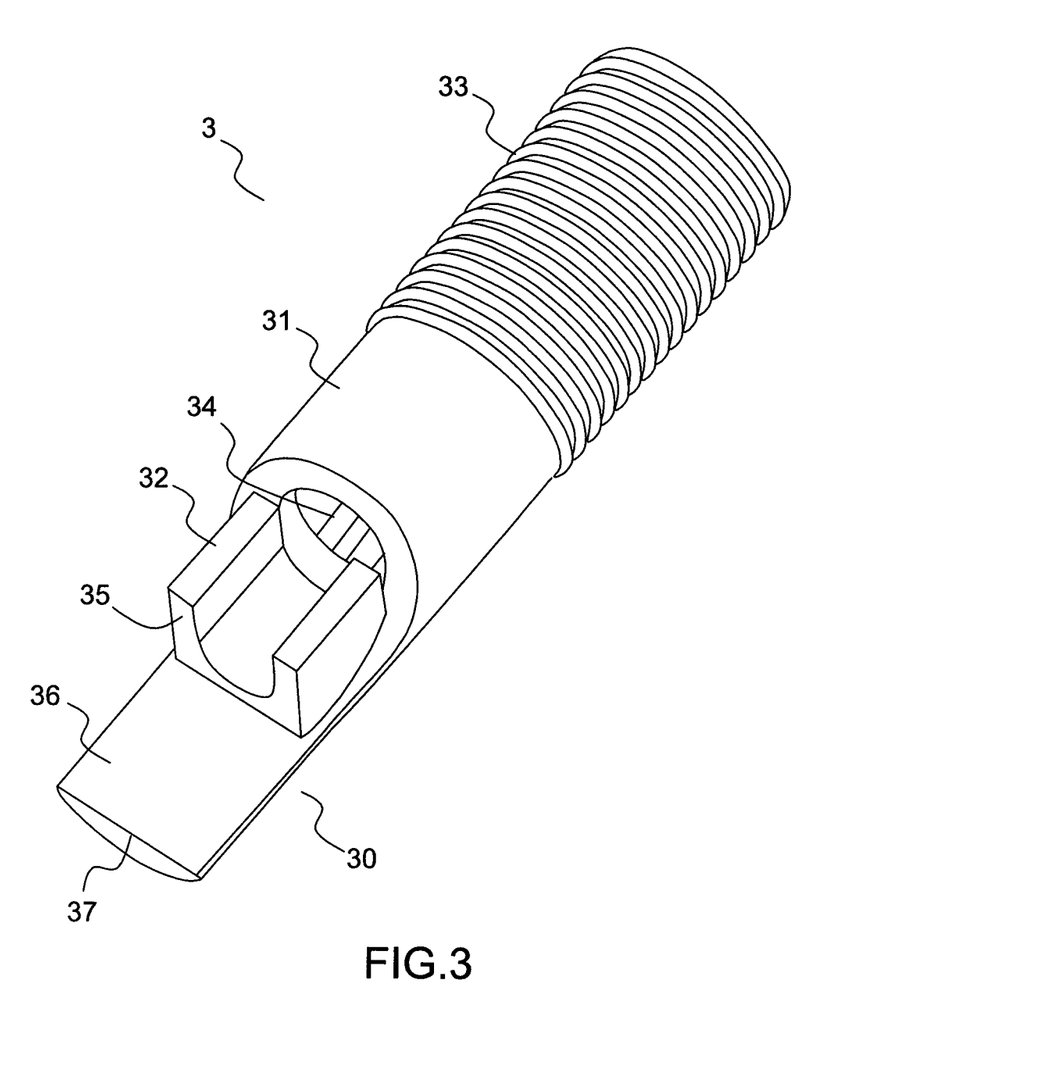
FIG. 3 represents a pusher mechanism of a miniaturized scanning system according to an embodiment.

The pusher mechanism 3 is adapted to engage with the abutment 2. In the embodiment as shown in FIGS. 3 and 6, it comprises an end portion 30 attached to a movable sleeve 31. The movable sleeve is mounted around the inner shaft 4 and configured to translate along the longitudinal axis Δ of the inner shaft and rotate along said axis, driving with him the end portion 30. The end portion comprises an edge 37 configured to be tangent to the external surface 20 of the abutment in operation, for example an edge of a surface 36 parallel to but distinct from the longitudinal axis Δ of the inner shaft. The edge 37 is configured to contact the external surface 20 at a given contact point. Translation of the movable sleeve along the longitudinal axis of the inner shaft causes the end portion to push against the abutment and thus to bend the abutment and the flexible device in a plane defined by the longitudinal axis Δ of the inner shaft and by the contact point between the external surface 20 of the abutment and the surface 36 of the end portion of the pusher mechanism. Rotation of the movable sleeve will thus result in a change of said contact point and thus a change in the bending plane. Rotation and translation may be driven independently or simultaneously. The movable sleeve 3 as shown in the example of FIG. 3 further comprises a guide 32 to engage with part 22 of the abutment 2 during translation of the movable sleeve. The abutment 20 may further be configured to limit the course of the translation of the movable sleeve. For that purpose, the abutment 2 may comprise a surface 20 to stop against the surface 35 of the guide 32.

In the example as shown in FIG. 6, the scanning mechanism further comprises an outer shaft 5 (represented in FIG. 5) to be mounted around the movable sleeve 31. The movable sleeve may be coupled to an inner surface 51 of the outer shaft to perform a helical movement with respect to the inner surface of the outer shaft, thus combining rotation and translation of the movable sleeve. For example, the helical movement is achieved by a screw system (33, 51) between the movable sleeve and the inner surface of the outer shaft. The translation may thus be proportional to the angle of rotation. The scanning system may further comprise a rotary drive mechanism of the movable sleeve around the longitudinal axis of the inner shaft. For example, the rotary drive mechanism comprises a toothed wheel (not shown) to be housed in a recess 41 of the inner shaft, wherein the toothed wheel is configured to be engaged with a toothed inner surface 34 of the movable sleeve 31. The rotary drive mechanism may further comprise a drive rod (not shown) passing through an opening 42 of the inner shaft to drive the toothed wheel. A driving motor positioned at a proximal part of the medical tool may rotate the toothed wheel using the drive rod. As shown in FIG. 4, the inner shaft 4 may comprise a recess 43 to help guiding the optical fiber cable in the distal end 44 of the groove.

The external surface 20 of the abutment may be calculated to determine the 2D movement of the end of the scanned device when the scanning mechanism is actuated. For example, the 2D movement may be a spiral.

The working principle of the miniaturized scanning system as shown in FIG. 6 is now explained with reference to FIGS. 7A and 7B to generate a spiral movement at a tip point P where the optical head (not shown in FIG. 7A, 7B) is located. In this example, the movable sleeve 31 describes a helical movement, driving the surface 36 of the end portion 30 attached to the movable sleeve. The external surface 20 of the abutment 2 is, for example, a conical surface. A cross sectional cut of said conical surface is shown for example in FIG. 8. The conical surface is defined by the relation between the parameters f and s as shown in FIG. 8. Said parameters of the conical surface may be determined in order to generate any desired form of spiral, for example an Archimedean spiral in which the radius is proportional to the angle of rotation.

Figure 7A:
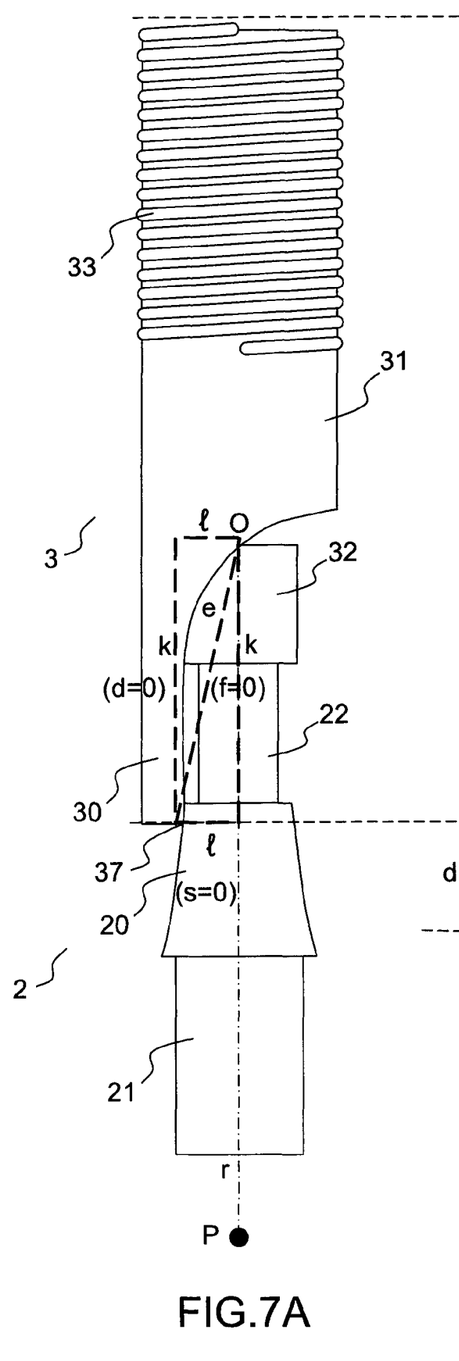
FIGS. 7A and 7B are schematic illustrations of the working principle using the miniaturized scanning system shown in FIG. 6.
Figure 7B:
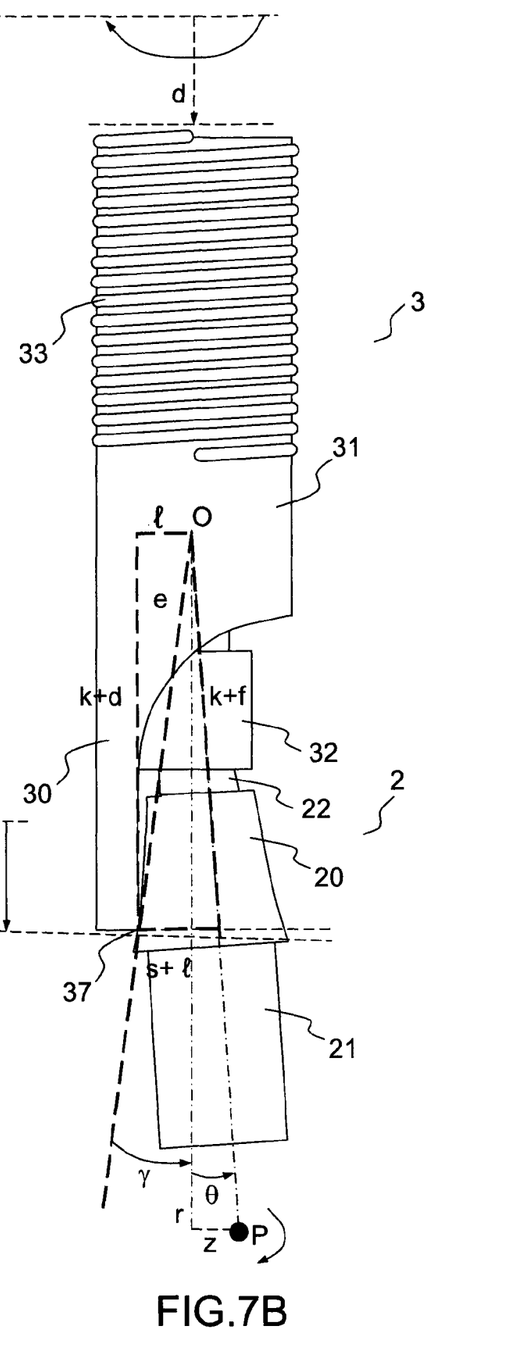
Figure 8:
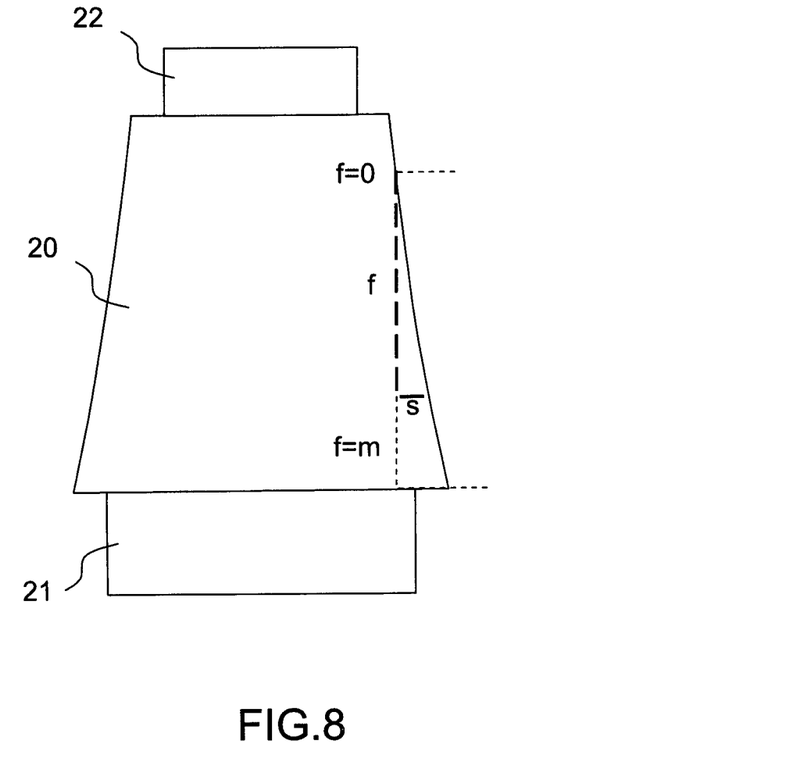
FIG. 8 represents an example of a conical external surface of an abutment according to an embodiment.

FIGS. 7A and 7B illustrate how the conical structure 2 generates the spiral motion in guidance of the pushing mechanism 3 pushing and rotating on the conical surface 20. In these figures the conical structure 2 is fixed to the point O. It can move around this point in two directions (pitch and yaw) but cannot turn around itself (no roll motion). This configuration is based on the assumption that for small angles of inclination ($\theta<10°$) a stiff cable, like the fiber optic cable, will bend exactly at the point it is fixed and the other parts will remain linear. It is also assumed that the conical structure is pressed on the end portion 30 of the pushing mechanism due to the resistance of the stiff fiber cable against bending. The optical fiber cable 12 passes through the centerlines of the movable sleeve 31 attached to the end portion 30 and conical structure 2.

In FIG. 7A, the pushing mechanism 3 is at its nominal position (d=0). The center-lines of the movable sleeve 31 and the conical structure 2 coincide. In this situation the tip point P is located at the center of the region to be scanned. In FIG. 7B, the movable sleeve is iterated (d>0). The end portion 30 pushes the conical surface 20. This causes the conical structure 2 to incline with an angle θ; as a result, the point P is translated by a distance $z=r \sin(\theta)$. The amount of the iteration d of the movable sleeve determines the amount of change in the tip position (z). When the movable sleeve is rotated, it translates the tip point P in xy dimensions along a circle with radius z. With changing the iteration of the movable sleeve (d), the radius of this circle changes. In this way a spiral motion is obtained.

The tip point P thus follows a trajectory passively constrained by the mechanics of the system. The precision of following the desired trajectory may thus be limited only by the precision of the mechanical construction of the pieces. In the embodiment as described in FIGS. 7A and 7B, it is only needed to rotate the moving sleeve to obtain the desired motion of the tip point P. This single rotation may be driven by a motor placed apart from the distal scanning system.

Figure 9A:
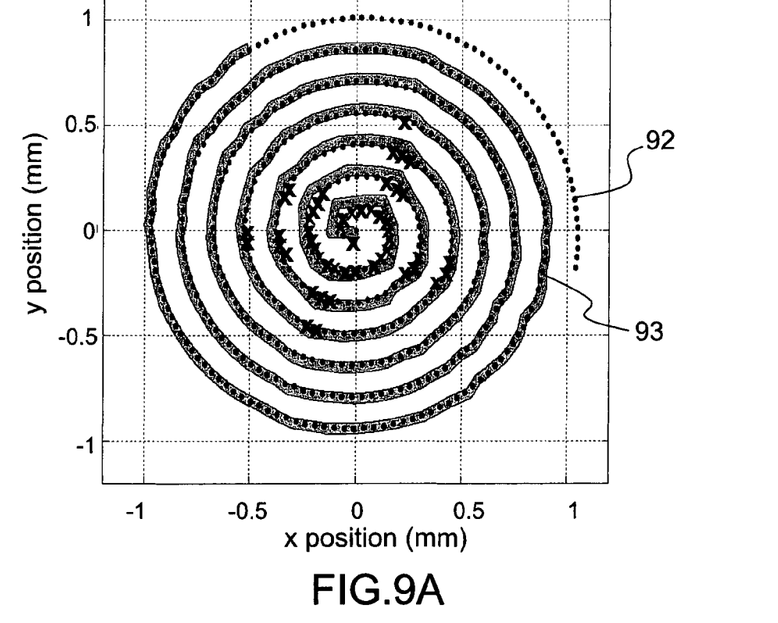
FIGS. 9A, 9B are images of a spiral drawn by an automated robot and a manual drive of a scale 5 prototype made according to an embodiment of the present disclosure, compared with an ideal Archimedean spiral.
Figure 9B:
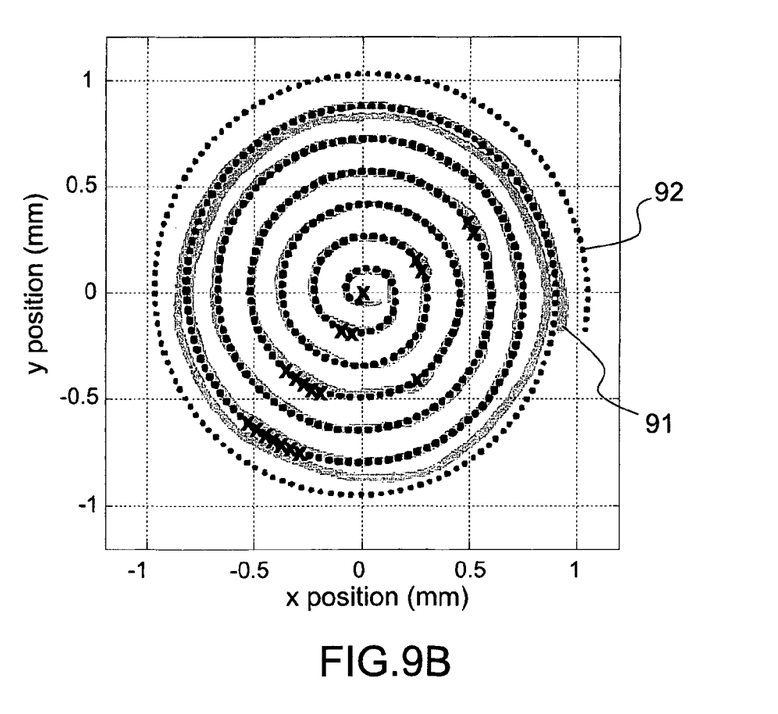

FIGS. 9A and 9B compare the spirals drawn respectively by the Stäubli® Robot and by a prototype of the scanning system as described in the present disclosure in order to quantify the degree of matching to an ideal Archimedean spiral. The prototype is a system as shown in FIG. 6 but with 5 times enlarged dimensions compared to a miniaturized scanning system to be used with a medical tool. A pencil is placed to the tip and spirals are drawn by driving manually the movable sleeve by rotating of the drive rod. In FIG. 9B, this image is reproduced as an image 91 in 5 times reduced dimensions and compared to the desired Archimedean spiral of the scale-1 dimension. The ideal spiral is indicated by dots 92 in FIG. 9B. In FIG. 9A, the drawing 93 corresponds to the spiral generated by the Stäubli® Robot in actual dimensions. On FIG. 9A is indicated again the ideal Archimedean spiral 92 (commanded trajectory). A comparison between the two systems is based on a measured average of points outside the 15 μm precision range to the total number of relevant points, these points being indicated by a cross in FIGS. 9A, 9B. This ratio is 0.89 with the Stäubli® Robot and 0.94 with the scanning system according to the present disclosure. This means that in the scale-5 dimensions, the scanning system according to the present disclosure can manage to follow the Archimedean spiral as good as the Stäubli® Robot doing in 1-scale dimension. The Stäubli® Robot has difficulty to follow the ideal spiral in the very central part, where large acceleration is required.

The present disclosure may be implemented for in-vivo imaging by integration to a fibered confocal microscope, for example the Cellvizio® imager from the Mauna Kea Technologies® (Paris, France). This system may perform confocal fluorescence imaging, records images of size 240×200 μm² with 1.2 μm lateral and 3 μm axial resolutions at a rate 12 frames/sec, and may use the mosaicing algorithm presented in US Patent Application 2009/0041314. The confocal probe may consist of a flexible bundle of optical fibers and an optic-head hosting the micro lenses, located at the tip. The outer diameter of the flexible bundle is 1.4 mm. The optic-head is for example a 12 mm long cylinder with an outer diameter of for example 2.6 mm.

The outer shaft is for example around 3.5 cm long with an inner diameter of 5 mm. In order to take images the surgeon manually brings the tip of the outer shaft to the locus of interest and slightly presses on the tissue. The outer edge of the outer shaft stabilizes the region to be scanned. The tissue covered by the edges of the outer shaft slightly bends and touches the tip of the optic-head inside. The surgeon presses a button to energize the motor that drives the movable sleeve. With the rotation of the movable sleeve the optic-head automatically scans the tissue following a spiral path. When the scan is completed, in approximately one minute, the driving motor stops and the surgeon is noticed with the turn-on of a led. At this point the scan is over and the images for mosaicing are collected. The surgeon releases the tube from the tissue and presses another button to initialize the system for another scan. This button activates the driving motor in the reverse direction to rewind to its initial position in about 5-10 seconds.

It is therefore possible with the miniaturized scanning mechanism of the present disclosure to scan an area of 3 mm² on the tissue. This corresponds to a circular region of approximately 2 mm in diameter. One minute duration is targeted for a full spiral scan. It corresponds to a linear speed of approximately 0.38 mm/sec on a spiral with 0.15 mm distance in between its sequential curves. The distance between the two successive scan-lines is restricted by the image size and should be less than 0.2 mm (200 μm).

As mentioned above, during scanning the outer shaft is pressed on the tissue. The outer shaft and the optic-head get into contact inside the tube. This contact may be maintained when the mechanism is moved inside the tube throughout the scan. With the conical structure 2 as described in FIG. 8 for example, the radius of scan is changed by inclination of the tip. At 1 mm radius of the spiral the change in the height of the tip is 0.025 mm, the inclination is 2.87 degrees. Both of the values remain in the acceptable range, less than 0.1 mm and less than 5 degrees, respectively, for keeping the tissue touching to the optic head.

Figure 10:
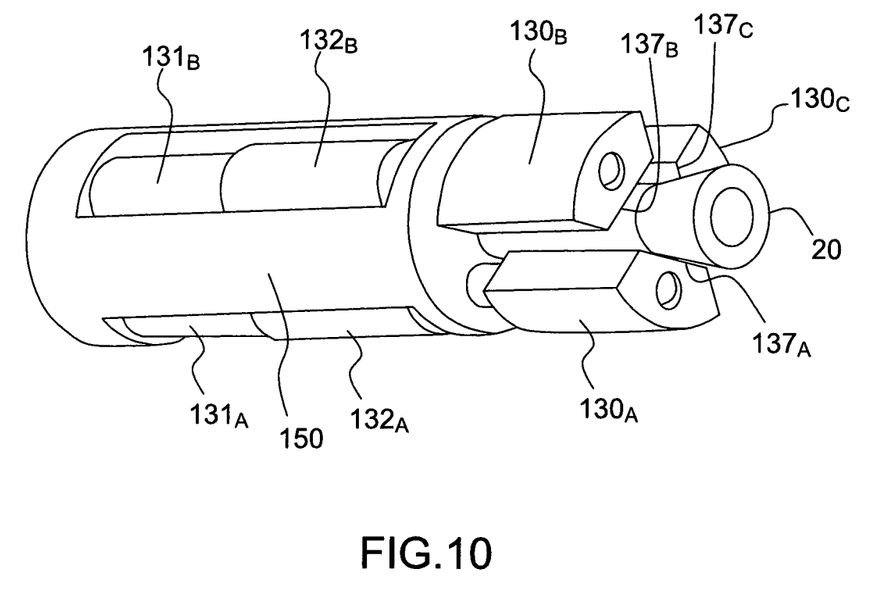
FIG. 10 represents another embodiment of a miniaturized scanning system.

FIG. 10 illustrates another embodiment of a miniaturized scanning system. It comprises an inner shaft (not shown in FIG. 10) to guide the flexible device along a longitudinal axis, an abutment adapted to maintain the flexible device (not shown) with an external surface 20, wherein said external surface may be for example an axially symmetric surface. It further comprises a pusher mechanism with at least two end portions configured to translate independently along a longitudinal axis of the inner shaft. In the example of FIG. 10, the pusher mechanism comprises three end portions 130A, 130B, 130C, each of which having an edge 137 to contact the external surface 20. The pusher mechanism further comprises for each end portion 130 a mechanism to drive said end portion in translation, for example a sliding system 131, 132. In the example of FIG. 10, translation of one of the end portion results in a bending of the flexible device in the plane defined by the longitudinal axis of the inner shaft and by the contact point between the edge 137 of the end portion 130 and the external surface 20. Driven conjointly the different end portions enables to define the motion of the tip point of the flexible part.

While the previous embodiment was described to generate movement of an optical probe, the mechanism of the miniaturized scanning device of the present disclosure is independent from the device characteristics and geometry. In particular, the miniaturized scanning device does not necessitate any special operation on the object to be manipulated and fixing the device at the abutment suffices. Consequently, the same could have been used to generate movement of any flexible device to be positioned at a distal part of a medical tool, or at least any device comprising a flexible portion, for example a hollow conduit (e.g. a catheter), a therapeutic device (e.g. a plasma jet, an electrode, surgical tools), an imaging device (e.g. optical probe for an endoscope, an endomicroscope).

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosed invention should be limited only by the attached claims.

What is claimed is:

1. A miniaturized scanning system to generate movement of a flexible device positioned at a distal part of a medical tool, comprising:
    a first shaft with a longitudinal axis, adapted to guide said flexible device along said longitudinal axis;
    an abutment comprising an external surface and adapted to maintain said device at the distal art of the medical tool; and
    a pusher mechanism adapted to engage with said abutment and comprising at least one end portion adapted to contact said external surface of the abutment at a contact point, wherein said end portion is configured to translate along said longitudinal axis of the first shaft and wherein the translation of said end portion results in a bending of the device in a bending plane defined by the longitudinal axis of the first shaft and said contact point.

2. The miniaturized scanning system according to claim 1, wherein the abutment comprises an axially symmetric structure to be mounted around said device.

3. The miniaturized scanning system according to claim 1, wherein the pusher mechanism comprises a movable sleeve with said end portion attached thereto, wherein the movable sleeve is mounted around said first shaft and configured to rotate around said longitudinal axis of the first shaft, the rotation of the movable sleeve resulting in a change of the contact point between said end portion and said external surface of the abutment.

4. The miniaturized scanning system according to claim 3, wherein said movable sleeve is configured to be simultaneously rotated around said longitudinal axis and translated along said axis.

5. The miniaturized scanning system according to claim 4 further comprising an outer shaft to be mounted around said movable sleeve, wherein said movable sleeve is coupled to an inner surface of the outer shaft to perform a helical movement with respect to said inner surface of the outer shaft.

6. The miniaturized scanning system according to claim 5, wherein said movable sleeve and inner surface of the outer shaft are coupled by a screw system.

7. The miniaturized scanning system according to claim 4, wherein said external surface of the abutment has a conical shape calculated such that the simultaneous rotation and translation movement of the movable sleeve results in a spiral motion of an end of the device.

8. The miniaturized scanning system according to claim 3, further comprising a rotary drive mechanism of the movable sleeve around said longitudinal axis of the first shaft.

9. The miniaturized scanning system according to claim 8, wherein the rotary drive mechanism comprises a toothed wheel arranged in a hollow portion of the first shaft and a drive rod.

10. The miniaturized scanning system according to claim 1, wherein said pusher mechanism comprises at least two end portions configured to translate independently.

11. The miniaturized scanning system according to claim 1, further comprising at least one driving motor to drive the at least one end portion of the pusher mechanism.

12. The miniaturized scanning system according to claim L, wherein said end portion comprises an edge configured to be tangent to the external surface of the abutment.

13. A robotized device comprising a flexible device to be positioned at a distal part of a medical tool and a miniaturized scanning system according to claim 1 to generate a movement of an end of said device.

14. The robotized device according to claim 13 wherein said flexible device is one of an imaging device, a therapeutic device, a hollow conduit.

15. A medical tool comprising:
a flexible device to be positioned at a distal part of said medical tool, and
a miniaturized scanning system according to claim 1 to generate a movement of an end of said device.

16. The medical tool according to claim 15, wherein said miniaturized scanning system comprises at least one driving motor positioned at a proximal part of the medical tool.

17. A fiber confocal microscopy system for inspecting a biological tissue comprising:
a confocal microscope with a distal part to be in contact with a biological tissue, wherein said distal part comprises an optical head connected to an optical fiber bundle,
a miniaturized scanning system according to claim 1 to generate a movement of said optical head.

18. The fiber confocal microscopy system according to claim 17, wherein the miniaturized scanning system comprises at least one driving motor positioned at a proximal part of the microscope.

19. A method for high resolution high field of view in vivo imaging of a biological using a confocal microscope with a distal part to be in contact with said biological tissue, wherein said distal part comprises an optical head connected to an optical fiber bundle, the method comprising:
moving said optical head using a miniaturized scanning system according to claim 1;
collecting images while said optical head is being moved; and
combining the collected images.

20. The method according to claim 19, wherein the motion of the optical head is a spiral motion.

* * * * *